United States Patent [19]
Sharp

[11] 3,962,821
[45] June 15, 1976

[54] POLLEN DISPENSING APPARATUS

[76] Inventor: David E. Sharp, Rte. 104, Ji-Meva Farms, North Rose, N.Y. 14516

[22] Filed: July 24, 1975

[21] Appl. No.: 598,717

[52] U.S. Cl. ............................. 47/1.41; 222/161; 222/174; 222/196.1
[51] Int. Cl.² ........................................ A01G 7/00
[58] Field of Search ............... 222/174, 161, 196.1; 47/1.41

[56] References Cited
UNITED STATES PATENTS

| | | | |
|---|---|---|---|
| 445,482 | 1/1891 | Waddill, Jr. | 222/161 |
| 2,802,302 | 8/1957 | Yost | 47/1.41 |
| 2,889,082 | 6/1959 | West | 222/161 |

*Primary Examiner*—Allen N. Knowles
*Assistant Examiner*—Hadd Lane
*Attorney, Agent, or Firm*—Charles S. McGuire

[57] ABSTRACT

Pollen is dispensed from a container through openings in a wall portion thereof by attaching the container to the end of a member which is manually movable by means of a handle at the end opposite the container. The member contacts a stop when moving in one direction, thereby agitating the pollen within the container so that it falls through the openings which are downwardly disposed when the handle is grasped.

5 Claims, 3 Drawing Figures

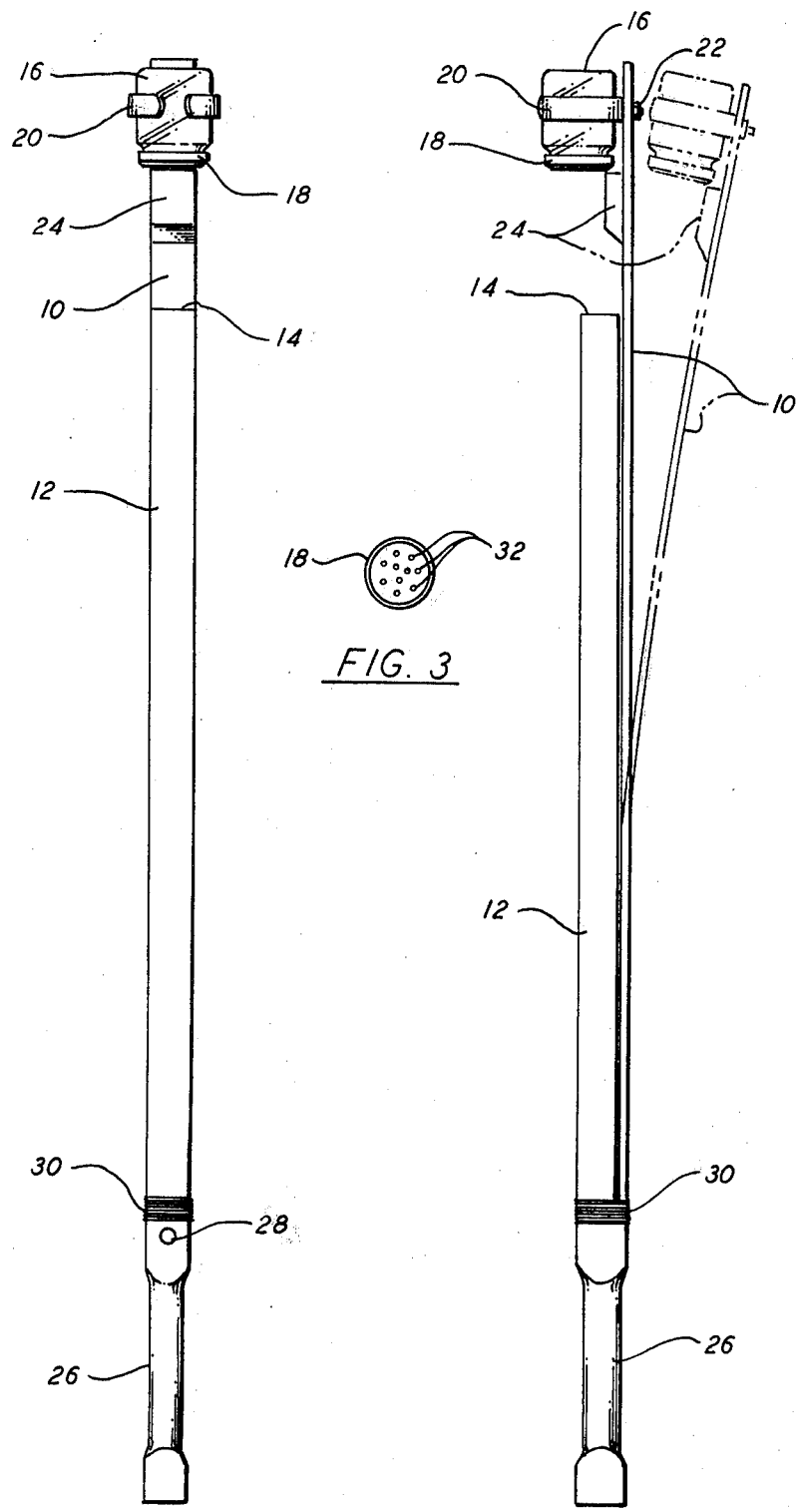

POLLEN DISPENSING APPARATUS

BACKGROUND OF THE INVENTION

The present invention relates to apparatus for dispensing pollen to be applied to plants such as fruit trees.

In the commercial growing of crops such as pears, apples, etc., better crop or fruit set may be obtained by cross pollination. Pollen is extracted from certain varieties of fruit trees and used to pollinate the buds of other trees by being released or dispensed in the vicinity thereof. Since the pollen is quite expensive, it is of course desirable to release it in a manner which provides the most efficient utilization thereof in terms of both the amount and uniformity of the released pollen which is ultimately effective. Prior dispensing techniques have included release from low-flying aircraft, bee hive inserts, firing from shotgun shells, etc. None of these means is entirely satisfactory since the operator cannot observe precisely where the dispensed pollen is going, and cannot control the amount of pollen dispensed in any given location.

It is a principal object of the present invention to provide apparatus for dispensing plant pollen into the air in a controllable and efficient manner.

A further object is to provide pollen dispensing apparatus which is single, inexpensive and easy to use.

Other objects will in part be obvious and will in part appear hereinafter.

SUMMARY OF THE INVENTION

Pollen which has been previously collected from a particular variety of plant, such as fruit trees, is placed in a container having a wall portion with perforations of suitable size to allow the pollen to escape when agitated within the container. The dispensing apparatus is provided with a handle at one end attached to an elongated member which is reciprocally movable by moving the handle back and forth. A stop is provided to limit travel of the elongated member in one direction. As the handle is moved back and forth the elongated member is abruptly stopped each time it makes contact with the limit stop. This agitates the pollen within the container attached to the elongated member and caused a small amount to be dispensed with each agitation.

The container is attached to the elongated member at a distance of preferably two or three feet from the handle. Thus, the pollen will be dispensed into the air at some distance above the head of an operator grasping the handle and moving it back and forth to cause the elongated member to contact the limit stop. The operator may walk past the trees, or other plants to be pollinated, and observe the rate and distribution of the pollen being dispensed. The rate of travel past the trees and/or the frequency of agitation of the container may be adjusted as desired to provide the proper rate and distribution of pollen which is carried to the buds by normal air currents.

BRIEF DESCRIPTION OF THE DRAWING

FIG. 1 is a front elevational view of a preferred embodiment of the pollen dispensing apparatus of the present invention;

FIG. 2 is a side elevational view of the apparatus of FIG. 1 showing portions thereof in two positions of movement; and FIG. 3 is a plan view of a portion of the apparatus.

DETAILED DESCRIPTION

The major portion of the apparatus may conveniently and economically be formed from a single piece of wood about three feet or more in length and about 1¼ inches square. The wood is sawed through lengthwise from one end to about 8 inches from the other end, and about ¼ inch from one side. This forms an elongated strip, denoted in the drawing by reference numeral 10, 1¼ inches wide and ¼ inch thick, joined at the end of the saw cut to the remaining portion, which will be about 1¼ inches wide and 7/8 inch thick, assuming about one-eighth inch to be removed by the saw cut. The remaining portion is hereinafter referred to as limit stop 12, and is cut off to form end 14, approximately 6 inches from the end at which the saw cut begins. Thus, elongated strip 10 is some 6 inches longer than limit stop 12.

Container 16, about 2 inches in diameter and having removable lid 18, is releasably attached by flexible clamp 20 to elongated strip 10 adjacent the free end thereof. Clamp 20 is secured to strip 10 by bolt 22, or any other convenient means. Block 24 is glued or otherwise secured to strip 10, or formed integrally therewith, to provide a stop against which lid 18 of container 16 abuts when the latter is held by clamp 20.

The end opposite that from which the saw cut is made is rounded off to form handle 26. Reinforcement is provided adjacent the end of the saw cut by bolt or screw 28, extending into or through the wood a short distance below the end of the saw cut, and by a binding 30 of wire, cord or tape approximately at the saw cut.

As shown in FIG. 3, lid 18 is provided with openings 32 of a size appropriate to the pollen to be dispensed. Container 16 is attached so that lid 18 is downwardly disposed when handle 26 is grasped and strip 10 held upright. Movement of handle 26 causes strip 10 flex from its base away from limit stop 12, as shown in phantom lines in FIG. 2. Upon return flexing movement strip 10 contacts limit stop 12, thereby stopping abruptly and agitating the pollen within container 16; causing a small amount to fall through openings 2. Thus, an operator walking or riding past trees or other plants may dispense pollen to be deposited therein at the desired rate while observing its distribution.

What is claimed is:

1. Apparatus for dispensing plant pollen to be carried through the air to plants in the vicinity of the apparatus, the latter comprising:
   a. a resilient, elongated support member having a base end and a free end;
   b. a container having a wall with perforations therein through which pollen may be dispensed and affixed to said support member adjacent said free end; and
   c. elongated handle means to which said support member is attached at said base end thereof, said handle means including a manually engagable portion extending from said base end away from said free end and a rigid portion extending in closely spaced relation to said support member from said base end toward said free end to the region of said container, whereby manipulation of said manually engagable portion causes flexure of said support member away from said rigid portion and return movement of said free end to strike said rigid portion with percussive effect to shake pollen from said container.

2. The invention according to claim 1 wherein said container wall having said perforations faces away from said free end, whereby when the apparatus is held with said free end pointing upward, said wall forms the lower end of said container.

3. The invention according to claim 2 wherein said wall comprises a removable lid of said container.

4. The invention according to claim 1 wherein said support member and said handle means are integrally formed from the same piece of material.

5. The invention according to claim 4 wherein said material is moved and said support member and said handle means are separated by a saw cut extending therebetween to said base end, the thicknesses of said support member and handle means providing the respective resilience and rigidity thereof.

* * * * *